(12) United States Patent
Webber

(10) Patent No.: US 7,473,229 B2
(45) Date of Patent: Jan. 6, 2009

(54) METHOD OF ANALYZING COMPONENTS OF ALVEOLAR BREATH

(75) Inventor: Michael Evan Webber, Culver City, CA (US)

(73) Assignee: Pranalytica, Inc., Santa Monica, CA (US)

(*) Notice: Subject to any disclaimer, the term of this patent is extended or adjusted under 35 U.S.C. 154(b) by 647 days.

(21) Appl. No.: 10/014,977

(22) Filed: Dec. 10, 2001

(65) Prior Publication Data

US 2003/0109795 A1 Jun. 12, 2003

(51) Int. Cl.
*A61B 5/02* (2006.01)
*G01N 1/22* (2006.01)
*G01N 31/00* (2006.01)
*G01N 33/497* (2006.01)

(52) U.S. Cl. .................. 600/532; 73/23.3; 422/84
(58) Field of Classification Search ......... 600/529–538; 73/23.3; 422/84
See application file for complete search history.

(56) References Cited

U.S. PATENT DOCUMENTS

| | | | | |
|---|---|---|---|---|
| 3,830,630 A | * | 8/1974 | Kiefer et al. | 73/23.3 |
| 4,316,380 A | * | 2/1982 | Heim et al. | 600/532 |
| 4,582,068 A | * | 4/1986 | Phillipps et al. | 600/529 |
| 4,809,810 A | * | 3/1989 | Elfman et al. | 600/532 |
| 5,376,555 A | * | 12/1994 | Forrester et al. | 42/84 |
| 5,445,160 A | * | 8/1995 | Culver et al. | 600/532 |
| 5,734,090 A | * | 3/1998 | Koppel et al. | 73/23.3 |
| 6,038,913 A | * | 3/2000 | Gustafsson et al. | 600/532 |
| 6,192,261 B1 | * | 2/2001 | Gratton et al. | 600/310 |

* cited by examiner

Primary Examiner—Robert L Nasser
(74) Attorney, Agent, or Firm—Jones Day (57) ABSTRACT

A method of analyzing alveolar breath. Breath is expired through an analysis chamber. The concentration of a first component of the breath is monitored as the breath is expired through the analysis chamber. When the concentration of the first component indicates that alveolar breath is in the analysis chamber, at least one concentration measurement of a second component of the breath is triggered. Concentration measurements of the second component are discontinued when the concentration of the first component indicates that alveolar breath is no longer passing through the analysis chamber.

31 Claims, 6 Drawing Sheets

METHOD OF ANALYZING COMPONENTS OF ALVEOLAR BREATH

BACKGROUND OF THE INVENTION

1. Field of the Invention

The field of the present invention is methods relating to the analysis of alveolar breath as it is expired.

2. Background

Most human adults have a lung capacity of approximately 5-6 liters. Of this capacity, approximately only 0.3 liters is involved with the exchange of gases between blood and breath which takes place in the alveoli. Within this 0.3 liters, called the alveolar breath, oxygen and nitrogen dioxide rapidly diffuse across the epithelial membrane separating blood from breath due to concentration gradients existing between the blood and breath. As a result, the concentration of many gaseous constituents in the alveolar breath closely reflect the partial pressure of the same constituents in blood.

Also present in alveolar breath are trace concentrations of molecules that are small enough to diffuse through the epithelial membrane. Some of these molecules have been shown to be indicative of disorders such as diabetes, lung cancer, and renal failure. Furthermore, depending on the severity of the disorder, such molecules may be present in alveolar breath in the parts per billion range (ppb) or in the parts per trillion range (ppt). Measurement of these trace components is therefore desirable for the early diagnosis of these disorders.

Measuring the concentration of these trace components in alveolar breath as the breath is expired requires determining when alveolar breath is present and being able to detect extremely minute amounts of the trace component. During respiration, of the six liter total lung capacity, only 0.5 liters (called the tidal volume) is exchanged with the ambient atmosphere. However, this 0.5 liters is not the only constituent of a normally expired breath. The first part of expired breath consists essentially of air from the mouth, nose, and upper respiratory tract. The next part of expired breath consists essentially of air from the bronchi and lower respiratory tract. Neither of these first two parts of expired breath includes gases that are exchanged with blood. Therefore, the concentration of a particular gas in either of these two parts does not necessarily reflect the partial pressure of that gas in the blood. The third and last part of expired breath consists essentially of alveolar breath. Alveolar breath is included in the 0.5 liters of tidal volume and contains gases that are exchanged with blood. Thus, the concentration of a gaseous component in alveolar breath closely reflects the partial pressure of that component in the blood.

Methods that are commonly employed to ensure that concentration measurements are being taken only from alveolar breath when it is expired are disclosed in U.S. Pat. No. 5,971,937 to Ekström. In general, Ekström discloses a method and device for measuring the concentrations of alcohol and carbon dioxide on expired breath using infrared spectrometry. In Ekström, the concentrations of alcohol and carbon dioxide in expired breath are periodically measured during expiration. Differences in the method disclosed in Ekström arise in determining when alveolar breath is present. When alveolar breath is determined to be present, the concentration measurements taken for alcohol are accepted as measurements that reflect the partial pressure of alcohol in the blood. All other alcohol concentration measurements are discarded as not reflecting blood alcohol levels.

A first method disclosed in Ekström relies on the volume of breath expired to identify the alveolar breath component of the expired breath. This method assumes that after a certain volume of breath has been expired, alveolar breath is subsequently expired and available for analysis. Breath volume, however, is not a reliable indicator of alveolar breath because breathing patterns and lung capacities vary between individuals. Additionally, the breathing pattern of a single individual may easily vary from breath to breath. Thus, because breath volume can vary so widely, it cannot be reliably used to identify alveolar breath during expiration.

A second method disclosed in Ekström relies on a predetermined amount of time passing before taking measurements of what is presumed to be alveolar breath. However, time is also not reliable to identify alveolar breath during expiration for the same reasons that volume is not reliable. Due to wide variations in breathing patterns, the expiration of alveolar breath cannot be accurately determined based upon the assumption that alveolar breath is expired after an individual exhales for a certain period of time.

A third method disclosed in Ekström is intended to eliminate false positive and false negative measurements of breath alcohol concentrations. Briefly, from the periodic alcohol and/or carbon dioxide concentration measurements, a change, or delta, in the concentrations is calculated between successively measured concentrations of each component. The delta is compared to a predetermined value to locate a plateau in the concentration level(s). The plateau is an indicator of the presence of alveolar breath. Once the plateau is detected, the alcohol concentration measurement taken at or near the time of the last carbon dioxide concentration measurement is accepted as a measurement of the concentration of alcohol in alveolar breath.

In the fourth method disclosed in Ekström, the concentration of carbon dioxide is compared to one or more predetermined values, the values establishing minimum and maximum concentration levels in normally expired breath. The minimum and maximum concentration levels are used to screen out inaccurate alcohol concentration measurements, which might result from hyper- or hypo-ventilation prior to expiring the breath being analyzed. If the carbon dioxide concentration falls within the specified minimum and maximum values, then the alcohol concentration measurement is accepted as an accurate reflection of alcohol in the alveolar breath.

In performing the method disclosed in Ekström, much data are taken that are duplicative or not needed for the concentration determination of alcohol in alveolar breath. For example, if the concentrations of both alcohol and carbon dioxide are monitored to detect the plateau, then one of the concentration measurements is redundant. Additionally, where every carbon dioxide concentration measurement must be compared to the threshold to identify alveolar breath, for those measurements that do not fall within the targeted thresholds, the corresponding alcohol measurements are useless and thus must be discarded.

Thus, an improved method of identifying and analyzing alveolar breath is needed. Such a method should enable alveolar breath to be detected and analyzed in a quick and straightforward manner without taking redundant or useless measurements. The method should also be flexible to accommodate the differences in the breathing patterns among different individuals and the breathing patterns of a single individual over several breaths.

SUMMARY OF THE INVENTION

The present invention is directed to a method for analyzing alveolar breath as it is expired. In a first separate aspect of the present invention, breath is expired through an analysis chamber. The concentration of a first component of the breath is continuously monitored as the breath passes through the chamber. The measured concentrations of the first component are used to determine when alveolar breath is present in the analysis chamber. Once alveolar breath is determined to be in the analysis chamber, one or more concentration measurements of a second component of the breath are triggered.

The first component is chosen such that its relative concentration allows discrimination between non-alveolar breath and alveolar breath. This method thus provides more efficient detection of the presence of alveolar breath and enables quick and accurate measurements of the concentration of the second component, while at the same time having the flexibility to adapt to different breathing patterns.

In a second separate aspect of the present invention, the first component may be carbon dioxide, oxygen, or water vapor.

In a third separate aspect of the present invention, each of the measured concentrations of the first component is compared to a threshold concentration to determine when alveolar breath is present in the analysis chamber. The threshold concentration may vary depending upon the particular first component being monitored. Where carbon dioxide is the first component, the threshold concentration preferably includes relative concentrations equal to or greater than 3.5%, and more preferably equal to or greater than 4.5%.

In a fourth separate aspect of the present invention, the threshold concentration is based upon a previous concentration measurement of the first component from a previous breath, preferably the immediately previous breath. Thus, the threshold concentration may be varied.

In a fifth separate aspect of the present invention, a laser is employed to measure the concentrations of the first and/or second components. Light having a first wavelength, corresponding to an absorption feature of the first component, and a second wavelength, corresponding to an absorption feature of the second component, is employed. The light at the first wavelength and the light at the second wavelength may travel separate and distinct paths or substantially similar paths within the analysis chamber. Where the latter option is employed, the light at the first and second wavelengths may be multiplexed into a single optical path prior to entering the analysis chamber.

In a sixth separate aspect of the present invention, the second component may be ammonia, nitric oxide, carbon dioxide, or an element selected from the chemical groupings of alcohols, alkanes, or ketones.

In a seventh separate aspect of the present invention, any of the foregoing aspects may be employed in combination.

Accordingly, it is an object of the present invention to provide a method for analyzing alveolar breath as it is expired. Other objects and advantages will appear hereinafter.

BRIEF DESCRIPTION OF THE DRAWINGS

In the drawings, wherein like reference numerals refer to similar components.

DETAILED DESCRIPTION OF THE PREFERRED EMBODIMENTS

Figure 1:
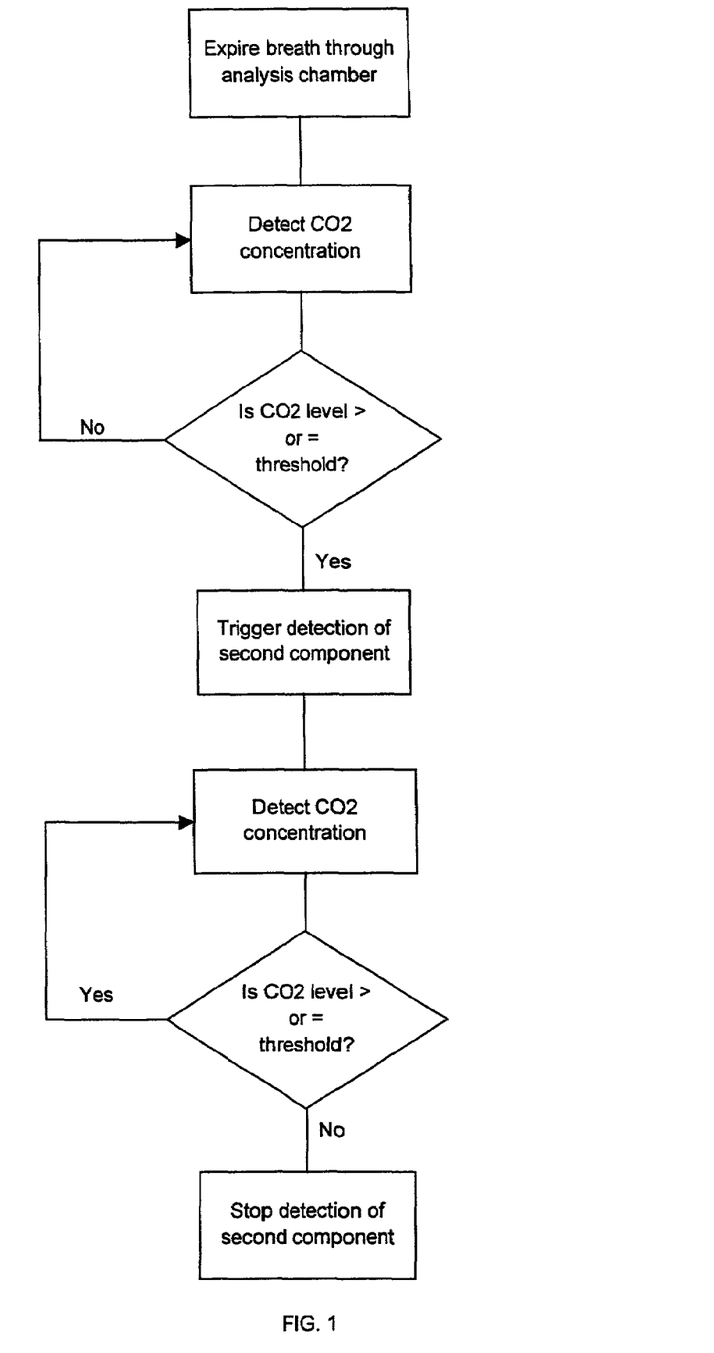
FIG. 1 is a logic diagram showing the operational process of the alveolar breath analyzing method in accordance with a preferred embodiment.

Turning in detail to the drawings, FIG. 1 is a flowchart illustrating the method of the present invention in accordance with a preferred embodiment. A single breath or a series of breaths are expired through an analysis chamber. The analysis chamber preferably has a small volume compared to the tidal volume of breath in an average individual. For example, since the average tidal volume is approximately 500 ml, the analysis chamber preferably has a volume of approximately 150 ml. The volume of the analysis chamber, however, may be smaller or larger depending on the lung capacity and alveolar breath expiration volume of the individual expiring into the analysis chamber.

As breath passes through the analysis chamber, the concentration of a first component is monitored to determine when alveolar breath is being expired. The first component may be any element or molecule shown to have a concentration profile in expired breath that enables the identification of alveolar breath. In FIG. 1, for purposes of example, the first component is carbon dioxide. Other elements or molecules may be monitored as the first component, including, for example, water vapor and oxygen.

The concentration of the first component is preferably monitored using a first spectrometer, although other techniques of monitoring the concentration of a gaseous component may also be employed. When the first component is carbon dioxide, the spectrometer preferably operates in the infrared spectrum. When other molecules are used as the first component, it may be desirable to have the spectrometer operate at other wavelengths, such as in the UV spectrum, visible spectrum, or near-infrared spectrum. The first spectrometer may employ any spectroscopy technique that is suitably sensitive to the levels of the first component in alveolar breath and has a response time that is fast enough to measure expired breath as the breath passes through an analysis chamber. Such spectroscopy techniques include, but are not limited to, absorption spectroscopy, photoacoustic spectroscopy, and cavity ring-down spectroscopy.

The first spectrometer may employ any light source that emits light at a wavelength that overlaps an absorption feature of the first component. Acceptable light sources emitting light in the infrared spectrum include, but are not limited to, halogen or tungsten lamps, laser diodes, or carbon dioxide lasers. If the light source used emits a broad spectrum, a wavelength filter is placed between the light source and the analysis chamber to pass light in a narrow spectrum that overlaps an absorption feature of the first component. When monitoring carbon dioxide as the first component, for example, the light used for the absorption measurement preferably overlaps an absorption feature of carbon dioxide, such as one of the many absorption transitions near the 2.0 µm wavelength. The operation and functionality of spectrometers are well known in the art, therefore the operation of the first spectrometer is only briefly addressed below.

Figure 2:
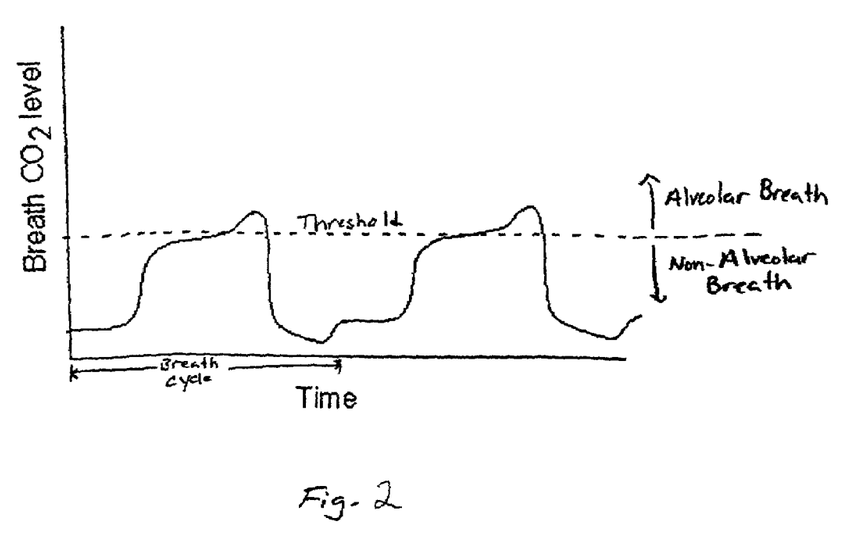
FIG. 2 is a graphical approximation of the carbon dioxide content in expired breath over time.

FIG. 2 graphically represents an approximation of the carbon dioxide concentration profile in expired breath over time. Alveolar breath is approximately represented in FIG. 2 where the concentration profile curve extends above the threshold represented by the dashed line. This threshold between non-alveolar breath and alveolar breath may vary from person to person, but for carbon dioxide it ranges from approximately 3.5% to 5.5% relative concentration or more at 1 atm of pressure of the expired breath.

Thus, in the case of carbon dioxide and other elements or molecules with similar concentration profiles, the expired breath is monitored to determine when the measured concentration exceeds the threshold. At this point, alveolar breath is present in the analysis chamber and analysis of the alveolar breath may proceed. However, for oxygen and other elements or molecules having concentration profiles that are approximately the inverse of carbon dioxide, alveolar breath is present when the concentration drops below the threshold.

Returning to FIG. 1, once the concentration of the first component indicates alveolar breath is being expired through the analysis chamber, the first spectrometer triggers at least one measurement of the concentration of a second component. Where multiple measurements of the second component are desired, measurements may continue until the concentration of the first component indicates that alveolar breath is no longer present in the analysis chamber. The second component may be any element or molecule contained in expired breath. Examples include ammonia, nitric oxide, carbon dioxide isotopes or molecules from chemical groups such as alcohols, alkanes, or ketones.

The concentration of the second component is preferably performed using a second spectrometer, although other techniques of monitoring the concentration of a gaseous component may also be employed. The first and second spectrometers are appropriately coupled to allow the first spectrometer to trigger the operation of the second spectrometer as described herein. As with the first spectrometer, the second spectrometer may use light in any appropriate spectrum, depending upon the absorption features of the second component, it may employ any appropriate spectroscopy technique, and it may employ any appropriate light source.

If the second component is expected to have only trace concentration levels, a laser spectrometer is preferably employed to achieve greater sensitivity. For even greater sensitivity, the methods taught in U.S. patent application Ser. No. 09/812,067, filed Mar. 19, 2001, the disclosure of which is incorporated herein by reference, may be utilized. When measuring the concentration of ammonia as the second component, for example, the light used for the absorption measurement preferably has a wavelength that overlaps an absorption feature of ammonia, such as one of the transitions near the 1532 nm wavelength. Except as noted, the second spectrometer may function in the same manner as the first spectrometer.

While the concentration of the second component is being measured, the monitoring of the concentration of the first component continues. Therefore, if carbon dioxide is the first component and alveolar breath is in the analysis chamber, when the concentration of carbon dioxide drops below the threshold alveolar breath is no longer present in the analysis chamber and concentration measurements of the second component are discontinued. Thus, the second spectrometer only measures the concentration of the second component while alveolar breath is present in the analysis chamber.

The threshold concentration value may be static or variable. A static threshold is set once at a particular level based upon the concentration profile of the first component and left at that level for subsequent breaths. Alternatively, the threshold may be variably dependent on the concentration profile of previously expired breaths, and preferably the threshold is dependent upon the concentration profile of the immediately previous expired breath. The process by which the threshold is adjusted may vary from simple to complex mathematical algorithms. For example, a simple adjustment may be made to the threshold by determining the highest (or lowest if the concentration profile warrants) relative concentration measured and subtracting (or adding) 0.5%. Thus, if the highest concentration of carbon dioxide measured was 5.5%, the new threshold would be set at 5.0%. Other more complex adjustments to the threshold are also contemplated. In this manner, the threshold is made flexible and can be adjusted to accommodate changes in breathing patterns.

In addition to measuring the concentration of the second component, the method may be easily adapted to simultaneously measure more than a single component in alveolar breath. Such may be accomplished, for example, by including additional spectrometers operating at appropriate wavelengths for the components being measured, each of which is triggered by the first spectrometer. Other methods of simultaneously measuring multiple components in alveolar breath are also contemplated.

Figure 3:
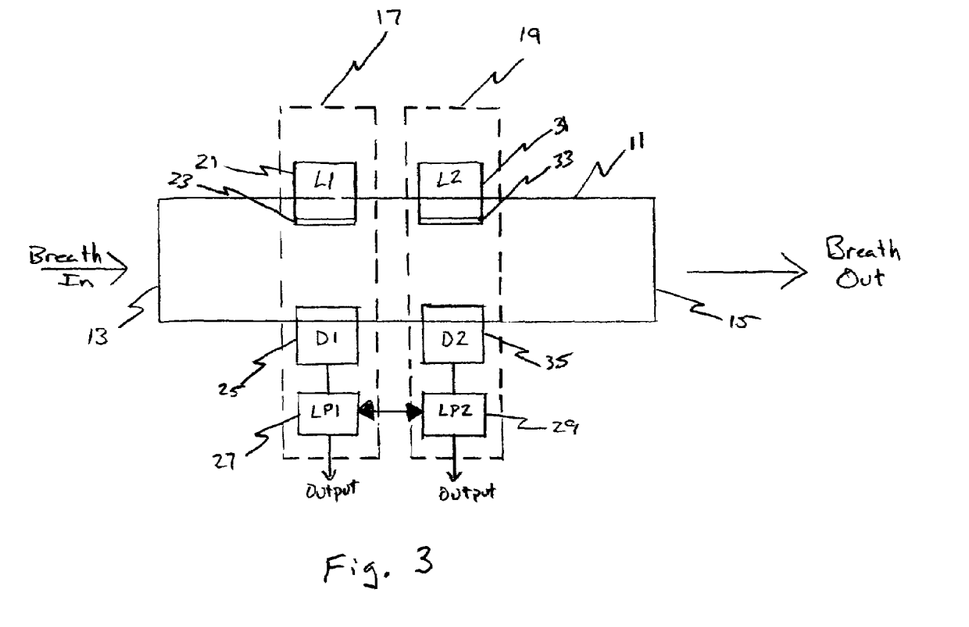
FIG. 3 is a side sectional view of a first apparatus, which may be employed in performing the alveolar breath analysis method.

FIG. 3 illustrates one embodiment of an apparatus that may be employed to perform the alveolar breath analysis described herein using absorption spectroscopy. The analysis chamber 11 includes an inlet 13 and an outlet 15 to allow expired breath to pass. First and second spectrometers 17, 19 are operatively connected to the analysis chamber 11 and communicably coupled to each other. The first spectrometer 17 includes a light source 21, a wavelength selector 23, and a light detector 25. Light from the source 21 is directed through the wavelength selector 23, into the analysis chamber 11, and towards the light detector 25. The wavelength selector 23 passes a wavelength that corresponds to an absorption feature of the first component. The wavelength should be selected as one that is not absorbed by the second component.

The light detector 25 periodically measures the power of the light after it has passed through the analysis chamber 11. The sampling rate of the light detector 25 may be adjusted to achieve the desired time response in detecting the presence of alveolar breath. Preferably, the power of the light is sampled approximately once every one-tenth of a second. Alternatively, the sampling rate may be made dependent on the breathing rate of the individual breathing into the collector. For example, during a first expiration into the analysis chamber 11, the individual's breathing rate, based on a single breath cycle, is measured. Thereafter, for each subsequent breath the sampling rate is a predetermined fraction of the previously measured breath rate. Additionally, the rate of each expired breath may be monitored, thus allowing the sampling rate to be adjusted for each subsequent breath. Adjustments to the sampling rate provide the breath analysis method with the adaptability to accommodate changes in breathing patterns.

The power of the light measured at the light detector 25 is converted into a concentration measurement by a logic processor 27 included with the first spectrometer 17. Converting the power measurement into a concentration of the first component requires initializing the logic processor 27 by taking power measurements when the analysis chamber 11 does not contain expired breath and when the analysis chamber 11 contains a known concentration of the first component. Initialization need not be done prior to every use of the apparatus if the first spectrometer 17 includes a memory in which the initialization values may be stored. Once the logic processor 27 is initialized, the concentration of the first component of expired breath may be determined according to the following equation:

$$\text{Concentration} = \text{constant} * \frac{P_0 - P_1}{P_0},$$

where $P_0$ is the power measurement when the analysis chamber does not contain expired breath and $P_1$ is the power measurement when expired breath is passing through the analysis chamber. The constant term is determined by using the power measurement from a known concentration of the first component and solving for the constant.

The logic processor 27 of the first spectrometer 17 is communicably connected to a logic processor 29 included with the second spectrometer 19 so that when alveolar breath is detected, the first spectrometer 17 may trigger the second spectrometer 19 to begin measuring the concentration of the second component. The second spectrometer 19 additionally includes a light source 31, a wavelength selector 33, and a light detector 35. The wavelength selector of the second spectrometer 19 passes light at a wavelength that corresponds to an absorption feature of the second component. If the wavelength at which the second infrared spectrometer operates is also absorbed by the first component, then the concentration of the first component measured by the first spectrometer 17 is used to offset the absorption measurement of the second spectrometer 19. In other respects, the second spectrometer 19 is operated in the same manner as described in connection with the first.

Figure 4:
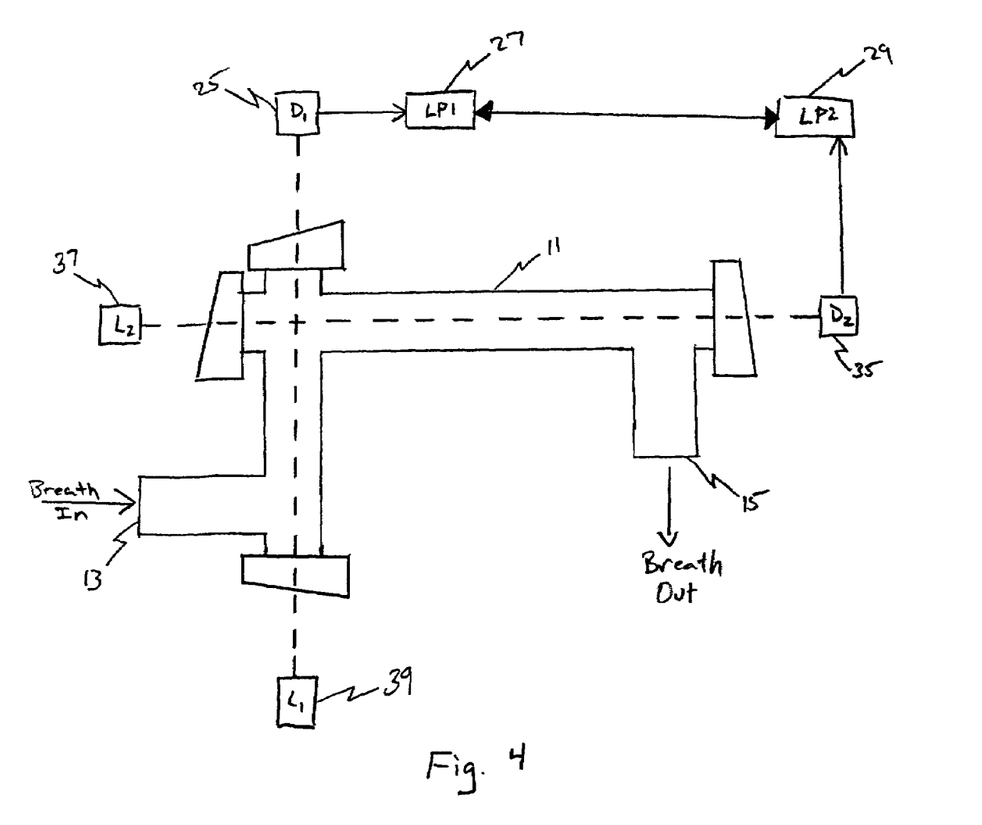
FIG. 4 is a side sectional view of a second apparatus, which may be employed in performing the alveolar breath analysis method.

FIG. 4 illustrates a second embodiment of an apparatus that may be employed to perform the alveolar breath analysis method described herein using absorption spectroscopy. The analysis chamber 11 again includes an inlet 13 and an outlet 15. The first spectrometer 17 comprises a laser diode 37 emitting light at a first wavelength that corresponds to an absorption feature of the first component. For purposes of example, this first wavelength may be near 2.0 μm for measuring carbon dioxide. Those skilled in the art will recognize that any type of laser may be utilized so long as it emits light at a wavelength that is absorbed by the first component. Again, however, the chosen first wavelength should not be absorbed by the second component, unless methods to distinguish the interfering signal are employed.

The second spectrometer comprises a laser diode 39 emitting light at a second wavelength that corresponds to an absorption feature of the second component. For purposes of example, this second wavelength may be near 1.5 μm for measuring ammonia. If the light at the second wavelength is also absorbed by the first component, then the concentration measurement performed by the first system may be used to subtract out the background absorption caused by the first component at the second wavelength. Again, those skilled in the art will recognize that any type of laser may be incorporated into the second spectrometer so long as it emits light at a wavelength that is absorbed by the second component.

The apparatus illustrated in FIG. 4 may be operated in the same manner as the apparatus in FIG. 3. However, should only trace concentrations of the second component be present in the expired breath, other more sensitive concentration measurement methods may be employed in conjunction with the apparatus of FIG. 4. Such methods include, for example, those disclosed in the aforementioned U.S. patent application Ser. No. 09/812,067, filed Mar. 19, 2001.

Figure 5:
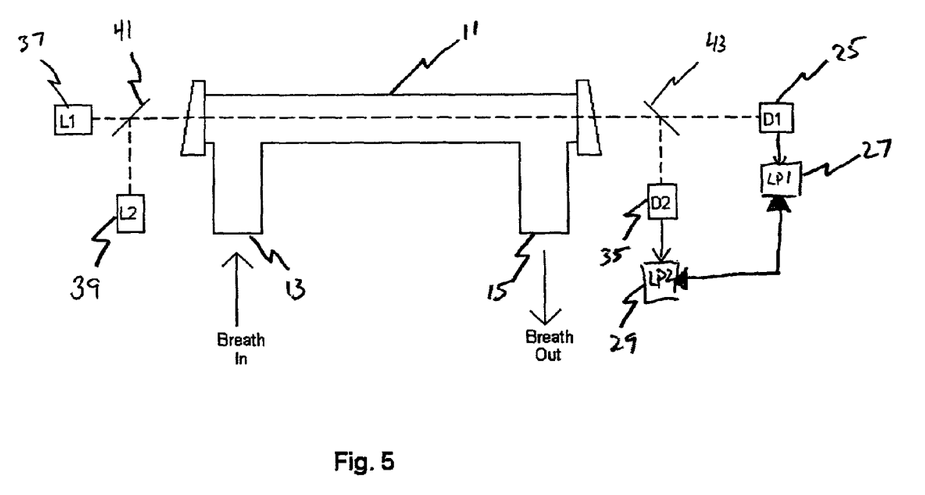
FIG. 5 is a side sectional view of a third apparatus, which may be employed in performing the alveolar breath analysis method.

FIG. 5 illustrates a third embodiment of an apparatus that may be employed to perform the alveolar breath analysis method disclosed herein using absorption spectroscopy. The apparatus in FIG. 5 operates in the same way previously described in association with FIG. 4. The primary difference in the apparatus of FIG. 5 is that light from the laser source is 37, 39 travel on substantially similar paths through the analysis chamber 11. This coincident optical path is accomplished by making the paths of the light emitted from each source intersect at a relative angle and placing a beam splitter 41 in paths at the point of intersection such that each beam is directed into the analysis chamber 11 from effectively the same point. After passing through the analysis chamber 11, the light is directed to a second beam splitter 43 which separates the two wavelengths. Each separated wavelength is directed towards a detector 25, 35 where the power of each separate beam is measured.

Figure 6:
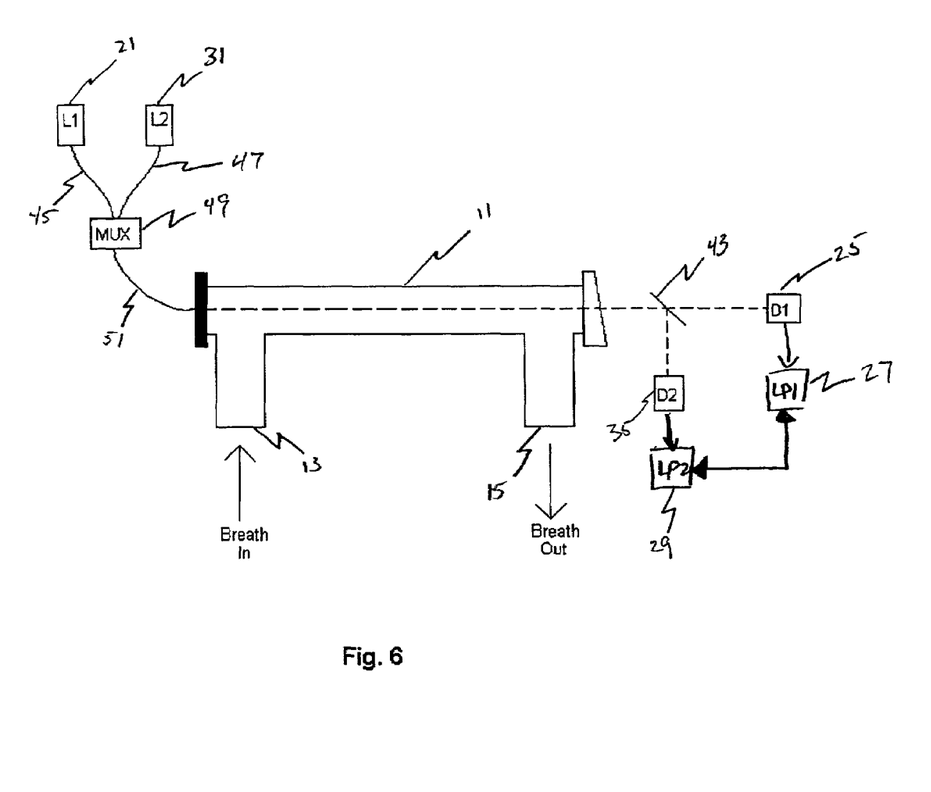
FIG. 6 is a side sectional view of a fourth apparatus, which may be employed in performing the alveolar breath analysis method.

FIG. 6 illustrates a fourth embodiment of an apparatus that may be employed to perform the alveolar breath analysis method described herein using absorption spectroscopy. The apparatus in FIG. 6 operates in the same way previously described in association with FIG. 4. The primary difference in the apparatus of FIG. 6 is that light from each laser is emitted into optical fibers 45, 47. The optical fibers 45, 47 guide the light into a multiplexing unit 49, where the light is multiplexed into a single optical fiber 51. The single optical fiber 51 guides the combined light into the analysis chamber 11. After passing through the analysis chamber 11, the light is directed to a beam splitter 43 which separates the two wavelengths. Each separated wavelength is directed towards a detector 25, 35 where the power of each separate beam is measured.

Thus, an alveolar breath analysis method is disclosed. While apparatuses have been described in connection with the alveolar breath analysis method, they are meant to serve as examples only for purposes of enabling the inventive concepts herein. It should be apparent to those skilled in the art that many more modifications and combinations are possible without departing from the inventive concepts herein. The invention, therefore, is not to be restricted except in the spirit of the following claims.

What is claimed is:

1. A method of analyzing alveolar breath comprising:
   expiring breath through an analysis chamber;
   continuously monitoring a concentration of a first component of the breath by measuring the light energy absorbed by the first component as the breath is expired through the analysis chamber to determine when alveolar breath is in the analysis chamber; and
   triggering at least one concentration spectroscopic measurement of a second component of the breath once the alveolar breath is in the analysis chamber, based on the concentration of the first component in only the immediately previous expired breath.

2. The method of claim 1, wherein triggering the at least one concentration measurement of the second component of the breath includes triggering the at least one concentration measurement when the concentration of the first component crosses a threshold concentration.

3. The method of claim 2, wherein the threshold concentration is at least 3.5% relative concentration of the first component.

4. The method of claim 2, wherein the threshold concentration is at least 4.5% relative concentration of the first component.

5. The method of claim 1, wherein the first component is carbon dioxide, oxygen, or water vapor.

6. The method of claim 1, wherein the second component is ammonia, nitric oxide, or a carbon dioxide isotope.

7. The method of claim 1, wherein the second component is an element selected from one of the following chemical groups: alcohols, alkanes, and ketones.

8. A method of analyzing alveolar breath comprising:
expiring breath through an analysis chamber;
continuously measuring a concentration of a first component of the breath expired through the analysis chamber means of measuring the light energy absorbed by the first component;
comparing each measured concentration of the first component to a threshold concentration to determine when alveolar breath is in the analysis chamber; and
triggering at least one concentration spectroscopic measurement of a second component of the breath once the alveolar breath is in the analysis chamber, based on the concentration of the first component in only the immediately previous expired breath.

9. The method of claim 8, wherein the threshold concentration is at least 3.5% relative concentration of the first component.

10. The method of claim 8, wherein the threshold concentration is at least 4.5% relative Concentration of the first component.

11. The method of claim 8, wherein the first component is carbon dioxide, oxygen, or water vapor.

12. The method of claim 8, wherein the second component is ammonia, nitric oxide, or a carbon dioxide isotope.

13. The method of claim 8, wherein the second component is a element selected from one of the following chemical groups: alcohols, alkanes, and ketones.

14. A method of analyzing alveolar breath comprising:
expiring breath through a analysis chamber;
passing light through the breath in the analysis chamber, the light comprising a first wavelength corresponding to a first absorption feature of a first component of the breath;
continuously measuring absorption of the light at the first wavelength by the first component to determine when alveolar breath is present in the analysis chamber; and
triggering at least one concentration spectroscopic measurement of the second component of the breath once the alveolar breath is in the analysis chamber, based on the concentration of the first component in only the immediately previous expired breath
wherein the light at the first wavelength and the light at the second wavelength are multiplexed prior to entering the analysis chamber.

15. The method of claim 14, wherein the light further comprises a second wavelength corresponding to a second absorption feature of the second component.

16. The method of claim 15, wherein the light at the first wavelength and the light at the second wavelength follow substantially similar paths in the analysis chamber.

17. The method of claim 14, wherein triggering the at least one concentration measurement of the second component of the alveolar breath in the analysis chamber includes triggering the at least one concentration measurement when the concentration of the first component crosses a threshold concentration.

18. The method of claim 17, wherein the threshold concentration is at least 3.5% relative concentration of the first component.

19. The method of claim 17, wherein the threshold concentration is at least 4.5% relative concentration of the first component.

20. The method of claim 14, wherein the first component is carbon dioxide, oxygen, or water vapor.

21. The method of claim 14, wherein the second component is ammonia, nitric oxide, or a carbon dioxide isotope.

22. The method of claim 14, wherein the second component is an element selected from one of the following chemical groups: alcohols, alkanes, and ketones.

23. A method of analyzing alveolar breath comprising:
expiring breath through an analysis chamber;
passing light through the breath in the analysis chamber, the light comprising a first wavelength corresponding to a first absorption feature of a first component of the breath;
continuously calculating a concentration of the first component of the breath by monitoring absorption of the light at the first wavelength by the first component;
comparing each calculated spectroscopic concentration of the first component to determine when alveolar breath is present in the analysis chamber; and
triggering at least one concentration measurement of the second component of the breath once the alveolar breath is in the analysis chamber, based on the concentration of the first component in only the immediately previous expired breath
wherein the light at the first wavelength and the light at the second wavelength are multiplexed prior to entering the analysis chamber.

24. The method of claim 23, wherein the light further comprises a second wavelength corresponding to a second absorption feature of the second component.

25. The method of claim 24, wherein the light at the first wavelength and the light at the second wavelength follow substantially similar paths in the analysis chamber.

26. The method of claim 23, wherein the threshold concentration is at least 3.5% relative concentration of the first component.

27. The method of claim 23, wherein the threshold concentration is at least 4.5% relative concentration of the first component.

28. The method of claim 23, wherein triggering the at least one concentration measurement of the second component of the alveolar breath in the analysis chamber includes triggering at least one spectroscopic measurement of the second component.

29. The method of claim 23, wherein the first component is carbon dioxide, oxygen, or water vapor.

30. The method of claim 23, wherein the second component is ammonia, nitric oxide, or a carbon dioxide isotope.

31. The method of claim 23, wherein the second component is an element selected from one of the following chemical groups: alcohols, alkanes, and ketones.

* * * * *